United States Patent [19]

Ebersole et al.

[11] Patent Number: 5,182,203
[45] Date of Patent: Jan. 26, 1993

[54] BIFUNCTIONAL COMPOUNDS USEFUL IN CATALYZED REPORTER DEPOSITION

[75] Inventors: Richard C. Ebersole, Wilmington, Del.; John R. Moran, Kennett Square, Pa.

[73] Assignee: E. I. Du Pont de Nemours and Company, Wilmington, Del.

[21] Appl. No.: 589,874

[22] Filed: Sep. 28, 1990

Related U.S. Application Data

[63] Continuation-in-part of Ser. No. 330,357, Mar. 29, 1989, abandoned, and a continuation-in-part of Ser. No. 494,226, Mar. 20, 1990, abandoned.

[51] Int. Cl.$^5$ .................... C12N 9/16; C12N 11/00; C12Q 1/00; G01N 33/534

[52] U.S. Cl. .................... 435/196; 435/7.9; 435/174; 435/964; 436/545; 436/546

[58] Field of Search ............... 435/196, 7.9, 174, 964; 436/545, 546

[56] References Cited

PUBLICATIONS

Chemical Abstracts, 106:210234n, 1987.

*Primary Examiner*—David M. Naff
*Assistant Examiner*—Mike Meller

[57] ABSTRACT

Novel bifunctional hydroxyphenylazobenzoic acid analogues (HABA-type and conjugates) and biotin analogues probiotin-type conjugates) useful as reagents in assays employing catalyzed reporter deposition are described as well as intermediates useful in synthesizing these compounds.

2 Claims, 3 Drawing Sheets

BIFUNCTIONAL COMPOUNDS USEFUL IN CATALYZED REPORTER DEPOSITION

RELATED APPLICATIONS

This application is a continuation-in-part of U.S. Ser. No. 07/330,357, filed Mar. 29, 1989 now abandoned, and U.S. Ser. No. 07/494,226 filed Mar. 20, 1990 now abandoned.

FIELD OF THE INVENTION

This invention relates to bifunctional compounds which are members of a specific binding pair and which possess a blocking group to prevent binding to the other member of the specific binding pair until such time as the blocking group is removed and possess a detectable label and, in particular, to bifunctional hydroxyphenylazobenzoic acid analogues (HABA-type and conjugates) and biotin analogues (probiotin-type conjugates) which are useful in assays in which the detector signal is amplified via catalyzed reporter deposition.

BACKGROUND OF THE INVENTION

The introduction of immunodiagnostic assays in the 1960s and 1970s greatly increased the number of analytes amenable to precise and accurate measurement. Radioimmunoassays (RIAs) and immunoradiometric (IRMA) assays utilize radioisotopic labeling of either an antibody or a competing antigen to measure an analyte. Detection systems based on enzymes or fluorescent labels were developed as an alternative to isotopic detection systems. Enzyme based assays proved to be more sensitive, faster, and less dependent upon expensive, sophisticated instrumentation.

The need for diagnostic assays having simpler formats, increased sensitivity with less dependence upon sophisticated and expensive instrumentation prompted investigators to try to harness the catalytic power of enzymes to develop these newer assays.

D. L. Bates, Trends in Biotechnology, pages 204-299, Vol. 5 No. 7 (1987), describes diagnostics which use a method of enzyme amplification to develop more sensitive and simple immunoassays. In this method a second enzyme system is coupled to the primary enzyme label, e.g., the primary enzyme can be linked catalytically to an additional system such as a substrate cycle or an enzyme cascade. Thus, the essence of enzyme amplification according to Bates is the coupling of catalytic processes wherein an enzyme is modulated by the action of a second enzyme, either by direct modification or by interaction with the product of the controlling enzyme.

U.S. Pat. No. 4,668,621, issued to Doellgast on May 26, 1987, describes application of an enzyme-linked coagulation assay (ELCA) to develop an amplified immunoassay using the clotting cascade to enhance sensitivity of detection of immune complexes. The process involves clot formation due to thrombin activated fibrin formation from insolubilized fibrinogen and labeled solubilized fibrinogen. Amplification of the amount of reportable ligand attached to solid phase is obtained only by combining use of clotting factor conjugates with subsequent coagulation cascade reactions. One of the disadvantages of this system is that it can only be used to measure the presence of materials which modulate the activity of one or more of the blood clotting factors. Another disadvantage is that the primary enzyme, thrombin, cannot be immobilized or coupled to a reporter or a member of a specific binding pair.

U.S. Pat. No. 4,463,090, issued to Harris on Jul. 31, 1984, describes a cascade amplification immunoassay requiring a combination of at least two sequential catalyses wherein a first enzyme activates a second enzyme which in turn acts upon the substrate.

Another amplification system is described in U.S. Pat. No. 4,598,042, issued to Self on Jul. 1, 1986, and U.K. Patent Application No. 2,059,421 which was published on Apr. 23, 1981, which disclose an immunoassay using an enzyme label to produce directly or indirectly a substance that is capable of influencing a catalytic event without itself being consumed during the catalytic event. More specifically, a primary enzyme system produces or removes a substance capable of modulating a secondary enzyme system which results in amplification. The enzyme systems use unconjugated enzymes to avoid the tendency to inactivate certain enzymes on conjugation.

European Patent Application Publication No. 123,265 which was published on Oct. 31, 1984, describes another cascade amplification immunoassay wherein a zymogen-derived-enzyme is coupled to a zymogen-to-enzyme cascade reaction sequence to obtain multiple stages of amplification in producing detectable marker material used to quantify analyte amount.

European Patent Application Publication No. 44,744, published Jun. 19, 1985, describes a specific binding assay based on enzyme cascade amplification wherein the label component employed in the detectant reagent is a participant in or a modulator of an enzyme cascade reaction wherein a first enzyme acts on a first substrate to product a second enzyme. The production of the second enzyme can be followed or the second enzyme can act on a second substrate to produce a third enzyme.

Similarly, U.S. Pat. No. 4,318,980, issued to Boguslaski et al. on Mar. 9, 1982, describes a heterogenous specific binding assay using a conjugate formed of a specific binding substance coupled to the reactant, i.e., an enzymatic reactant. The ability of the reactant to participate in the monitoring reaction to detect the presence of analyte is altered by the presence of the ligand in the medium. Thus, the conjugate in its free state is more active in the monitoring reaction than in its bound state.

A heterogenous specific binding assay using enzyme amplification is described in British Patent Application No. 1,401,297 which was published on Jul. 30, 1975 and U.S. Pat. No. 4,376,825, issued to Rubenstein et al. on Mar. 15, 1983. Amplification is achieved by bonding the compound to be assayed or a counterfeit of it to an enzyme. The resulting enzyme-bound-ligand competes with free ligand for specific receptor sites. When the enzyme-bound ligand is displaced by the free ligand the enzyme is then free to react with a large number of substrate molecules and the concentration of the remaining substrate or of the product can be measured. PCT International Publication No. WO 81/00725 which was published on Mar. 19, 1981 describes a method of determining a substrate in a sample which comprises converting the substrate to a product in a first stage of a cyclic reaction sequence and converting the product back to the substrate in a second reaction stage of the cyclic reaction sequence. At least one of the first and second reaction stages is enzyme catalyzed.

PCT Application having International Publication Number WO 84/02193, which was published on Jun. 7, 1984, describes a chromgenic support immunoassay wherein the analyte is contacted with an enzyme-labeled antibody and in which the signal generated by the reaction of the enzyme with its substrate is concentrated on an active support.

European Patent Application Publication No. 181,762, published on May 21, 1986, describes a method to determined enzymatic activity in a liquid sample by particle agglutination or inhibition of particle agglutination.

Substrate/cofactor cycling is another example of amplification which is based on the cycling of a cofactor or substrate which is generated by the primary enzyme label. The primary enzyme converts the primary substrate to an active form which can be cycled by two enzymes of the amplifier cycle. These two enzymes are provided in high concentration and are poised to turn over high concentrations of substrate but are prevented from so doing until the cycling substrate is formed. The product of the primary enzyme is a catalytic activator of the amplifier cycle which responds in proportion to the concentration of substrate and hence the concentration of the enzyme label.

In the early sixties, Lowry et al., Journal of Biological Chemistry, pages 2746-2755, Vol. 236, No. 10 (October 1961), described the measurement of pyridine nucleotides by enzymatic cycling in which the coenzyme to be determined was made to amplify an enzymatic dismutation between two substrates.

A more complex substrate cycling system is described in U.S. Pat. No. 4,745,054, issued to Rabin et al. on May 17, 1988. The Rabin system involves using a small enzymically inactive peptide fragment of an enzyme as a label and conjugated with the complementary fragment to form an enzyme which catalyzes a primary reaction whose product is, or leads to, an essential coenzyme or prosthetic group for a second enzyme which catalyzes a secondary reaction leading to a detectable result indicating the presence of analyte. Vary et al., Clinical Chemistry, pages 1696-1701, Vol. 32 (1986) describe an amplification method suited to nucleic acids. This is the strand displacement assay which uses the unique ability of a polynucleotide to act as a substrate label which can be released by a phosphorylase.

SUMMARY OF THE INVENTION

This invention concerns novel bifunctional conjugates comprising a substrate which is a member of a specific binding pair and which is constructed to possess 1) a blocking group which prevents binding with the other member of the binding pair until such time as the blocking group is removed or activated and 2) a detectable label. These conjugates are useful in assays in which the detector signal is amplified via catalyzed reporter deposition.

HABA-type conjugates are compounds having the formula:

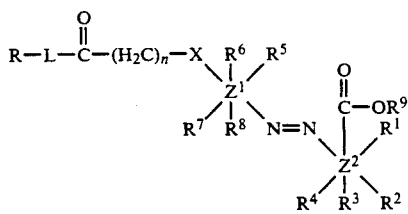

wherein:

$R^1$ through $R^8$ are the same or different and are selected from the group consisting of H, OH, $OCH_3$, straight chain or branched alkyl groups having 1-4 carbon atoms, F, Cl, Br or I;

$Z^1$ and $Z^2$ are independently phenyl or naphthyl;

n is 1-19;

X is N, O, S;

$R^9$ is selected from the group consisting of glycosides and straight chain or branched alkyl groups having 1-4 carbon atoms;

L is $(NH(CH_2)_sCO)_r$ where s is 1-5 and r is 0-5; and

R is a reporter selected from the group consisting of radioisotopes, fluorogenic, light scattering, chemiluminescent, electrochemical and magnetic materials or enzymes provided that the enzyme does not react with $OR^9$.

Probiotin-type conjugates are compounds having the formula:

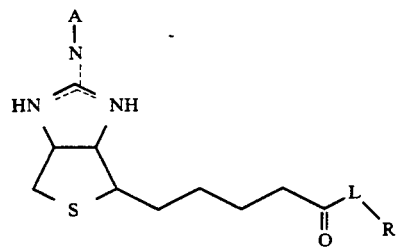

wherein

A is an enzymatically cleavable moiety which, after cleavage, leaves a biotin analogue capable of binding with avidin;

L is $(NH(CH_2)_sCO)_r$ where s is 1-5 and r is 0-5; and

R is a reporter selected from the group consisting of radioisotopes, fluorogenic, light scattering, chemiluminescent, electrochemical and magnetic materials or enzymes provided that the enzyme does not react with A.

In another embodiment this invention concerns intermediates useful in synthesizing these conjugates.

DETAILED DESCRIPTION OF THE INVENTION

Figure 1:
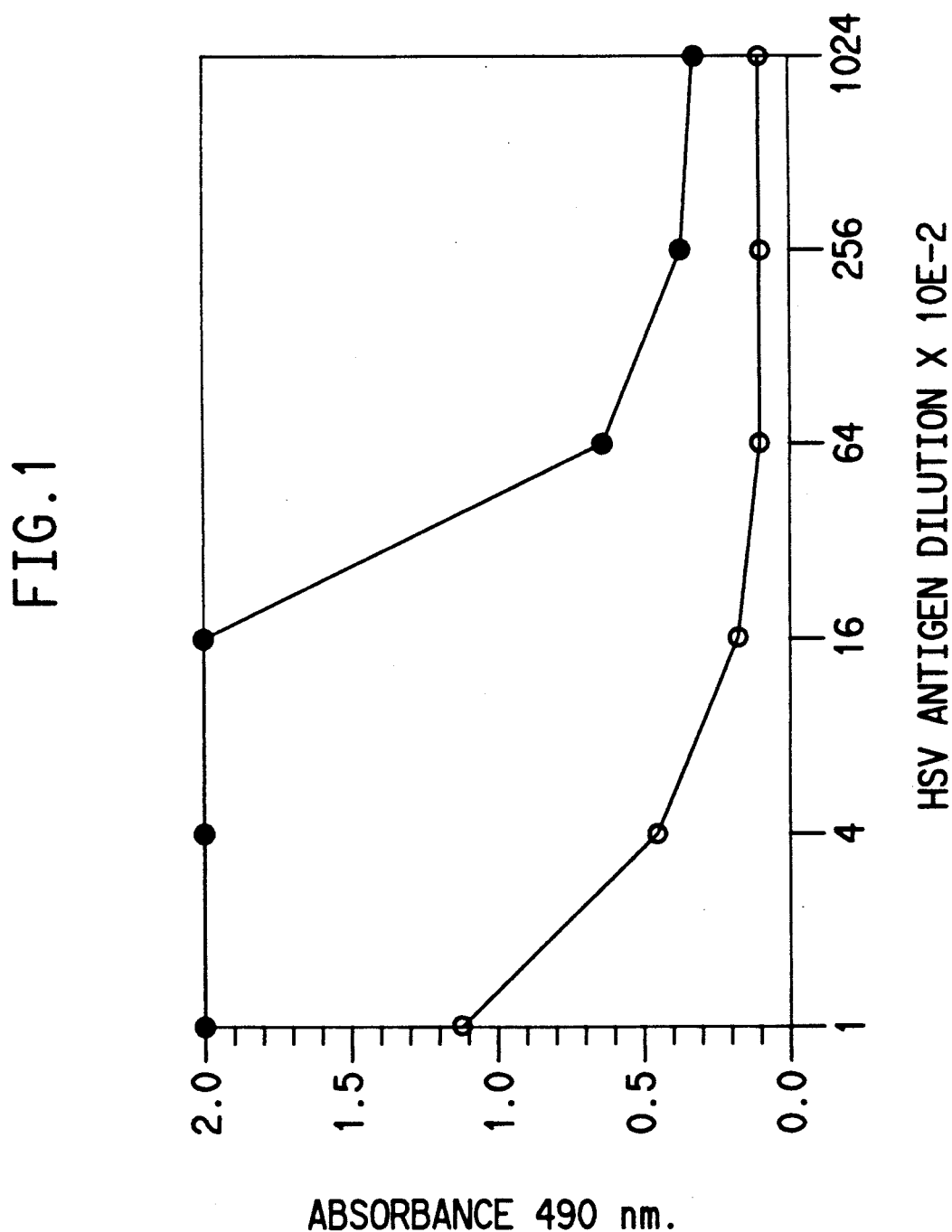
FIG. 1 is a graph comparing results of an HSV antigen assay run with and without catalyzed reporter deposition.

The term analyte dependent enzyme activation system (ADEAS) refers to an enzyme system wherein (i) at least one enzyme is coupled, in any manner known to those skilled in the art, to a member of a specific binding pair, or (ii) the enzyme need not be coupled to a member of a specific binding pair when it is the analyte. The enzyme, either by itself or in connection with a second enzyme, catalyzes the formation of an activated conjugate which then is deposited wherever a receptor for the activated conjugate is immobilized.

The term amplification as used herein means amplification of reporter signal due to deposition of a conjugate activated by an ADEAS.

The term conjugate means a detectably labeled substrate specific for the ADEAS whether it be a single enzyme ADEAS or multi-enzyme ADEAS. The substrate must have at least one component but is not limited to such. For example, the substrate can consist of two components. One component contains the binding site for the receptor and is detectably labeled. The other component is a constituent which prevents or interferes with binding to the receptor until such time as the ADEAS primes the conjugate as is discussed below. Another example of a conjugate is biotin-tyramine wherein tyramine is the substrate portion and biotin constitutes the detectable label as described below. Conjugates are described in greater detail below as well.

The term detectably labeled means that the substrate can be coupled to either a reporter or to an unlabeled first member of a specific binding pair provided that the reporter introduces a different moiety to the substrate as is discussed below. When the substrate is coupled to an unlabeled member of a specific binding pair, following deposition, the substrate-specific binding partner complex is reacted with the second member of the binding pair which is coupled to a reporter. Alternately, the substrate-specific binding partner complex can be pre-reacted with the detectably labeled other member of the specific binding pair prior to deposition.

The term deposition means directed binding of an activated conjugate to the receptor which results from the formation of a specific binding pair interaction as described below.

The term receptor means a site which will bind to the activated conjugate either through the formation of a specific binding pair interaction as described below.

The term activated conjugate means that the conjugate has been primed by the ADEAS to bind with the receptor.

The term HABA-type conjugate means HABA derivatives: (i) which can be substituted or unsubstituted and are coupled with or without a spacer to a reporter and (ii) which contain an ADEAS activatable moiety that prevents the conjugate from binding to streptavidin until it has been activated or removed by the ADEAS.

The term probiotin-type conjugate means probiotin derivatives: (i) which can be substituted or unsubstituted and are coupled with or without a spacer to a reporter and (ii) which contain an ADEAS activatable moiety that prevents the conjugate from binding to a biotin binding receptor (e.g., streptavidin, avidin) until it has been activated or removed by the ADEAS.

One of the unique features of this invention is the analyte dependent enzyme activation system which catalyzes deposition of conjugate by converting the substrate portion of the conjugate to an activated form which is deposited wherever a specific receptor for the activated conjugate is immobilized. The ADEAS does not utilize enzyme cascade reactions or enzyme cycling to effect amplification. Rather, it uses either a single enzyme or combination of enzymes to activate the conjugate. Deposition of conjugate occurs only if the analyte and analyte dependent enzyme activation system, which can be the same if the analyte is an enzyme, for example in the detection of an enzyme such as alkaline phosphatase, or different, have been reacted and a receptor, as described below, is immobilized to bind the activated conjugate. Thus, the ADEAS, conjugate, and receptor are chosen to form an operational trio.

The following is one embodiment of a single enzyme ADEAS system applied to a forward sandwich immunoassay format: the test sample containing the analyte is reacted with an immobilized capture reagent, such as an antibody; excess reagents are washed off; the immobilized capture antibody-analyte complex is reacted with an ADEAS, such as a second antibody specific for the analyte which has been coupled to an enzyme, e.g. horseradish peroxidase (HRP), alkaline phosphatase (AP), etc. The ADEAS will bind only if the analyte has been bound by the capture reagent. Otherwise the reagents will be washed off. Coupling of the enzyme to a specific binding partner does not affect the enzyme's ability to react with the substrate portion of the conjugate. When conjugate such as biotin-tyramine or HABA-tyramine analog (e.g., N-(4'''-hydroxyphenethyl)-6-(phenoxy-(4'-azo-2''-benzoic acid))hexamide) is added to the immobilized capture antibody-analyte-second antibody-enzyme complex, the enzyme reacts with the substrate portion of the conjugate, e.g., with the tyramine portion of the conjugate, converting it to an active form which will bind to an immobilized receptor which is either endogenous or exogenous to the assay system. The amount of conjugate deposited will be a function of immobilized ADEAS. Deposited conjugate such as biotin-tyramine or HABA tyramine analog can then be detected by reacting with streptavidin-HRP and orthophenylenediamine. The term HABA-tyramine analog means, generally, unsubstituted or substituted HABA, coupled with or without a spacer, to a hydroxy-phenyl containing compound such as tyramine. If the conjugate is fluorescein-tyramine then the deposited conjugate can be detected directly, or following reaction with a labeled anti-fluorescein antibody.

Figure 3:
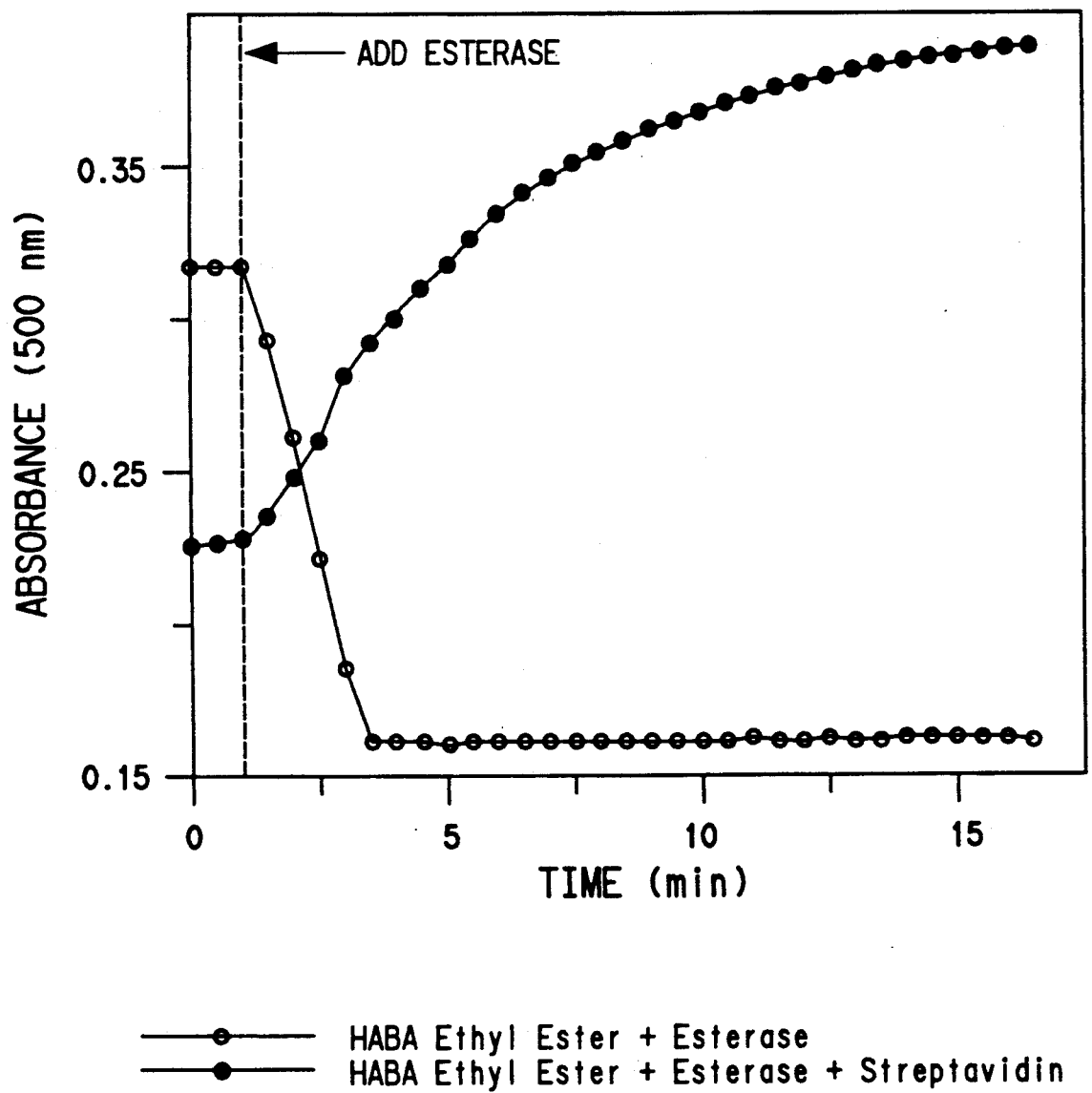
FIG. 3 illustrates the esterase catalyzed conversion of HEE to HABA and the subsequent binding of HABA to form the 2-(4'-hydroxyphenylazo)benzoic acid (HABA)/streptavidin complex.

Thus, the ADEAS is used to catalyze the deposition of detectably labeled substrate (the conjugate) to generate additional signal. The ADEAS is detected directly as part of the overall signal when the enzyme component of the ADEAS is the same as the enzyme used as the reporter. FIG. 3 illustrates this situation as well as the situation where an ADEAS enzyme component and reporter enzyme are different and thus, the ADEAS enzyme component is not detected directly as part of the overall signal.

A multi-enzyme ADEAS immunoassay format would involve a similar approach. For example, the ADEAS can be an antibody coupled to an enzyme such as neuraminidase. In addition to the immobilized capture antibody-analyte-second antibody-neuraminidase complex, a second enzyme such as $\beta$-galactosidase is added together with the conjugate. The conjugate can be a detectably labeled moiety containing a sialyl-galactosyl glycoside. Neuraminidase releases the terminal sialic 20 acid residue which then enables β-galactosidase to remove the galactose group. Without the release of the terminal sialic acid residue, the β-galactosidase cannot remove the galactose group. Once deglycosylation is complete, the activated conjugate deposits wherever receptors for the activated conjugate are immobilized.

The instant invention is surprising and unexpected because amplification of reporter signal is obtained via deposited activated conjugate without using cascade mechanisms or enzyme cycling. The ADEAS reacts with the conjugate to form an activated conjugate which will bind with immobilized receptor specific for the activated conjugate. The amounts of receptor and activated conjugate are in excess of the amount of ADEAS immobilized.

The choice of an ADEAS is governed by the ability of the enzyme or enzymes to convert a conjugate to an activated form which will bind to an immobilized receptor whether endogenous or exogenous. Accordingly, a detailed knowledge of catalytic properties of each specific enzyme is needed in order to properly design the substrate and receptor. Other important factors include availability of the enzyme or enzymes, relative ease or difficulty of coupling it to the member of a specific binding pair, stability of the enzyme or enzymes as well as the stability of the conjugate and the receptor. In some cases, an ADEAS can be purchased, depending on the assay format.

Enzymes suitable for use in an ADEAS include hydrolases, lyases, oxidoreductases, transferases isomerases and ligases. There can be mentioned peroxidases, oxidases, phosphatases, esterases, and glycosidases. Specific examples include alkaline phosphatase, lipases, beta-galactosidase, horseradish peroxidase, and porcine liver esterase.

Members of specific binding pairs suitable for use in practicing the invention can be of the immune or non-immune type. Immune specific binding pairs are exemplified by antigen/antibody systems or hapten/antihapten systems. The antibody member, whether polyclonal, monoclonal or an immunoreactive fragment thereof, of the binding pair can be produced by customary methods familiar to those skilled in the art. The terms immunoreactive antibody fragment or immunoreactive fragment mean fragments which contain the binding region of the antibody. Such fragments may be Fab-type fragments which are defined as fragments devoid of the Fc portion, e.g., Fab, Fab' and F(ab')$_2$ fragments, or may be so-called "half-molecule" fragments obtained by reductive cleavage of the disulfide bonds connecting the heavy chain components of the intact antibody. If the antigen member of the specific binding pair is not immunogenic, e.g., a hapten, it can be covalently coupled to a carrier protein to render it immunogenic.

Non-immune binding pairs include systems wherein the two components share a natural affinity for each other but are not antibodies. Exemplary non-immune binding pairs are biotin-avidin or biotin-streptavidin, folic acid-folate binding protein, complementary probe nucleic acids, etc. Also included are non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters sulfonyl halides, and coupler dyes such as 3-methyl-2-benzothiazolinone hydrazine (MBTH) and 3-(dimethylamino)benzoic acid (DMAB), etc.

Suitable supports used in assays include synthetic polymer supports, such as polystyrene, polypropylene, substituted polystyrene, e.g., aminated or carboxylated polystyrene; polyacrylamides; polyamides; polyvinylchloride, etc.; glass beads; agarose; nitrocellulose; nylon; polyvinylidenedifluoride, surface-modified nylon, etc.

Another important component of the invention is the conjugate, i.e., a detectably labeled substrate which must be specific for the ADEAS. As was stated above, when the conjugate reacts with the ADEAS, the enzyme or enzymes catalyze formation of an activated conjugate which binds wherever a receptor is immobilized whether exogenous or endogenous. The activated conjugate binds to the receptor via a specific binding pair interaction as described above. An immobilized exogenous receptor means a receptor which does not originate within the assay. It must be immobilized on the surface of the support prior to adding the conjugate to the reaction mixture. An endogenous receptor means a receptor which originates within the assay and does not require immobilization prior to adding the conjugate because the receptor is immobilized within the assay system.

For example, when an HRP ADEAS (HRP coupled to a member of a specific binding pair) is reacted with conjugate containing a phenolic substrate, an activated phenolic substrate is produced. It is believed that the activated phenolic substrate binds to electron rich moieties such as tyrosine and tryptophan present in the proteins on the solid support. However, if a different conjugate is used, such as a labeled MBTH which is discussed below, a receptor, such as an analog of DMAB, must be immobilized prior to addition of conjugate.

Another embodiment involves reacting a conjugate which becomes phosphorylated by an ADEAS. The activated (phosphorylated) conjugate can then react with an antibody specific for the activated conjugate.

In still another variation, an ADEAS can be reacted with a conjugate consisting of a component which when activated will bind to a receptor and which is coupled to a component having a thiol reactive group such as a maleimide. The deposited maleimide moiety can then be detected by reacting with a sulfhydryl-containing reporter which can be endogenous to the reporter, e.g., beta-galactosidase, or the sulfhydryl groups can be added to reporters such as HRP or AP using thiolating reagents such as N-succinimidyl-S-acetylthioacetate (SATA), S-acetylmercaptosuccinic anhydride (SAMSA), or succinimidyl-3-(acetylthio)-propionate (SATP).

Alternatively, the substrate can be coupled to a protected sulfhydryl containing group and this can be used as the conjugate. After binding to the receptor, this can be deprotected using conventional techniques known to those skilled in the art. Detection can be effected using a reporter having a thiol reactive group such as maleimide-HRP or iodoacetyl-HRP.

Another alternative is to use a conjugate wherein the substrate has two components as described above, a detectably labeled first component which will bind to the receptor after the second component has been activated or removed by the ADEAS.

The bifunctionality of the conjugate comprising a substrate containing a blocking group and a detectable label requires that careful consideration be given to its molecular construction. Specifically, the blocking group must be selected so that binding between the conjugate and the receptor (second member of the binding pair) is effectively blocked or inhibited. This is accomplished by synthetically modifying the substrate through the attachment of a blocking group. Synthetic modification is carried out in a region of the substrate molecule essential for attachment to its receptor. It is also essential that the blocking group be enzymatically cleavable or activated by the ADEAS so that, once removed or activated, the substrate can bind to the receptor.

In addition, the substrate should contain a site which permits attachment of a reporter. Generally, this is accomplished by synthetically attaching a reporter at a region of the substrate molecule not involved in binding to the receptor. For large reporters such as an enzyme, the attachment may or may not require the use of a molecular spacer. Generally, the nature of the chemical attachment of the reporter should be such that it is not affected by the ADEAS.

The compounds of this invention constitute such bifunctional conjugates, specifically, these are novel HABA-type conjugates and probiotin-type conjugates and intermediates for synthesizing these compounds.

2-(4'-hydroxyphenylazo)benzoic acid (HABA) is a small organic molecule which binds to avidin and streptavidin. (It should be noted that the terms avidin and streptavidin are used herein interchangeably.) HABA can be detectably labeled with or without a spacer using any of the reporters described below, e.g., radioisotopes, enzymes, etc. For instance, alkaline phosphatase (AP) can be conjugated to HABA, using techniques well known to those skilled in the art, with or without a spacer, to a functional group on HABA. An example of such a functional group is the 4'-hydroxyl moiety.

Moreover, HABA analogues can be modified to possess a second component which prevents binding until it has been removed by the ADEAS. For example, esterification of HABA with ethanol produces a HABA ethyl ester which does not bind to streptavidin. Detectably labeled HABA ethyl esters will not bind to streptavidin until the ester group has been hydrolyzed to the corresponding carboxylic acid. Hydrolysis can be affected using an enzyme such as an esterase, e.g., porcine liver esterase. Thus, detectably labeled HABA esters such as 6-(phenoxy-(4'-azo-2''-carboxyethylphenyl)-hexanoylalkaline phosphatase can be deposited using an ADEAS having a suitable esterase which will hydrolyze the ester to permit binding of detectably labeled HABA with streptavidin (i.e., exogenous receptor) which has been immobilized on the surface of a support.

HABA-type conjugates of the invention have the formula:

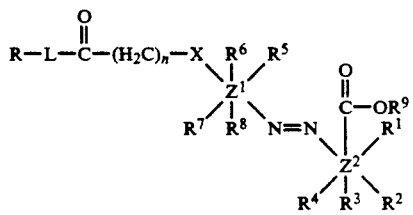

wherein:
$R^1$ through $R^8$ are the same or different and are selected from the group consisting of H, OH, OCH$_3$, straight chain or branched alkyl groups having 1-4 carbon atoms, F, Cl, Br or I;

$Z^1$ and $Z^2$ are independently phenyl or naphthyl;

n is 1-19;

X is N, O, S;

$R^9$ is selected from the group consisting of glycosides and straight chain or branched alkyl groups having 1-4 carbon atoms;

L is $(NH(CH_2)_sCO)_r$ where s is 1-5 and r is 0-5; and

R is a reporter selected from the group consisting of radioisotopes, fluorogenic, light scattering, chemiluminescent, electrochemical and magnetic materials or enzymes provided that the enzyme does not react with $OR^9$.

These HABA-type conjugates can be synthesized using conventional techniques well known to those skilled in the art from compounds having the formula:

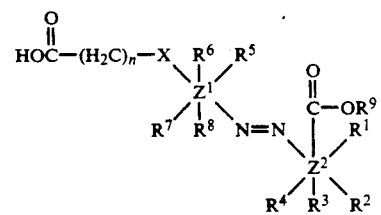

wherein
$R^1$ through $R^8$ are the same or different and are selected from the group consisting of H, OH, OCH$_3$, straight chain or branched alkyl groups having 1-4 carbon atoms, F, Cl, Br or I;

$Z^1$ and $Z^2$ are independently phenyl or naphthyl;

n is 1-19;

X is N, O, S; and $R^9$ is selected from the group consisting of H, glycosides, straight chain or branched alkyl groups having 1-4 carbon atoms.

The above-described intermediates can be further modified using techniques well known to those skilled in the art to produce compounds of the formula

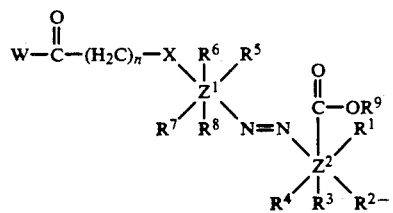

wherein:
$R^1$ through $R^8$ are the same or different and are selected from the group consisting of H, OH, OCH$_3$, straight or branched alkyl groups having 1-4 carbon atoms, F, Cl, Br or I;

$Z^1$ and $Z^2$ are independently phenyl or naphthyl;

n is 1-19;

X is N, O, or S;

$R^9$ is selected from the group consisting of H, glycosides, straight chain or branched alkyl groups having 1-4 carbon atoms; and W is selected from the group consisting of

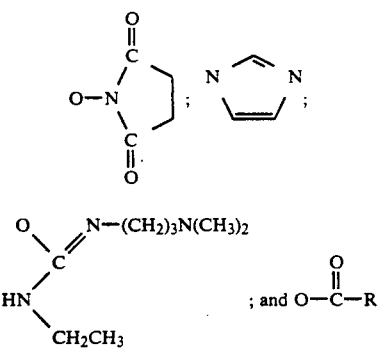

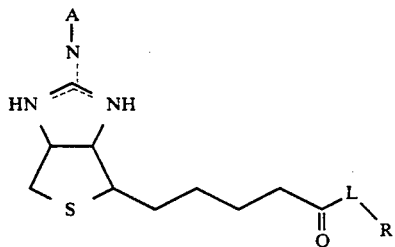

where R is a straight chain or branched alkyl group having 1-4 carbon atoms.

The approach described below in the examples can be modified by those skilled in the art generally to synthesize any of these compounds using conventional procedures.

In another embodiment this invention concerns a new class of biotin analogues which are referred to herein as probiotin-type conjugates which have the general formula:

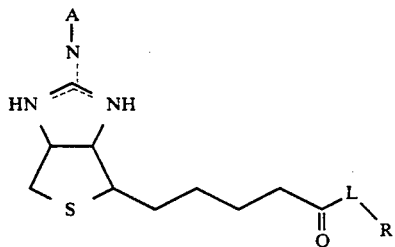

wherein

A is an enzymatically cleavable moiety which, after cleavage, leaves a biotin analogue capable of binding with avidin;

L is $(NH(CH_2)_sCO)r$ where s is 1-5 and r is 0-5; and

R is a reporter selected from the group consisting of radioisotopes, fluorogenic, light scattering, chemiluminescent, electrochemical and magnetic materials or enzymes provided that the enzyme does not react with A.

These probiotin-type conjugates are constructed to have a different functionality at two sites in the molecule as described above: 1) a functionality capable of being detectably labeled and 2) a functionality capable of being derivatized with a blocking group which prevents the probiotin-type conjugate from binding to biotin receptors until the blocking group is activated or removed by the ADEAS.

For example, the C2' position is designed to provide for introduction of a blocking group capable of suppressing the binding of the analogues to biotin receptors (avidin, streptavidin ... etc.) until activated or removed by an ADEAS. Once activated or deblocked these conjugates possess affinity for biotin receptors and bind to the receptor. Generally, blocking is achieved by derivatizing the C2' position with alkylesters, phosphates, glycosides, oligosaccharides or through formation of peptide bonds with amino acids and polypeptides. Such blocking groups include carboxylic esters, phosphoric acid esters, sulfuric acid esters, carboxylic acid amides, phosphoric acid amides, sulfuric acid amides, glycosides, benzyl ethers and benzyl amides. Cleavage of the blocking moieties can be achieved using enzymes such as oxidases, transferases, ligases, lyases, isomerases, hydrolases.

The C10 position is available for attaching a detectable label using techniques well known to those skilled in the art. Many types of reporters including radioisotopes, fluorogenic, light scattering, chemiluminescent, electrochemical and magnetic materials or enzymes can be used.

For example, the C10 carboxylic can be activated using any commonly known technique such as reaction with carbodiimides, carbonyldiimidazole, etc. The activated intermediate can then be coupled with or without a spacer to a variety of enzymes or chemical reporters containing free amine groups. Conventional linking conditions, reported in the art for coupling an enzyme to NHS biotin, also can be employed to couple NHS probiotins to an enzyme reporter such as alkaline phosphatase, horseradish peroxidase, $\beta$-galactosidase, and glucose oxidase.

It is important in selecting a suitable reporter enzyme that it not react with the blocking group A which is activated or removed by the ADEAS.

The following are examples of probiotin derivatives which can be detectably labeled using conventional techniques and examples of the enzyme which can be used to activate the compounds to bind with avidin. As used herein, the term probiotin derivative means a biotin derivative containing one functionality, specifically, an ADEAS activatable moiety that prevents binding to a biotin binding receptor until it has been activated or removed by the ADEAS. In these examples the probiotin derivatives are modified at the C2' position.

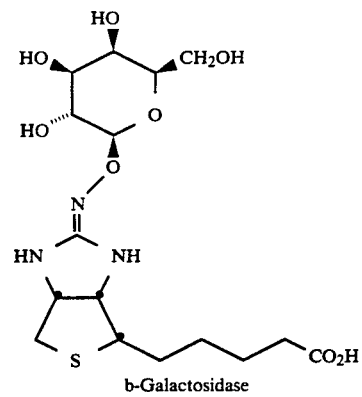

b-Galactosidase

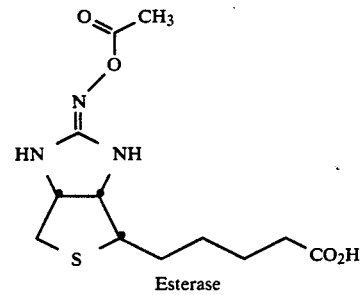

Esterase

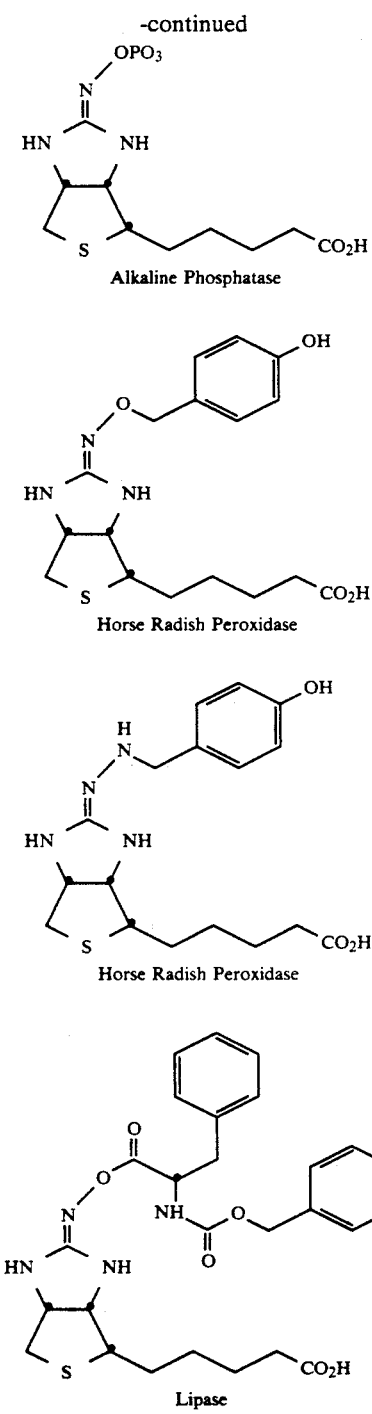

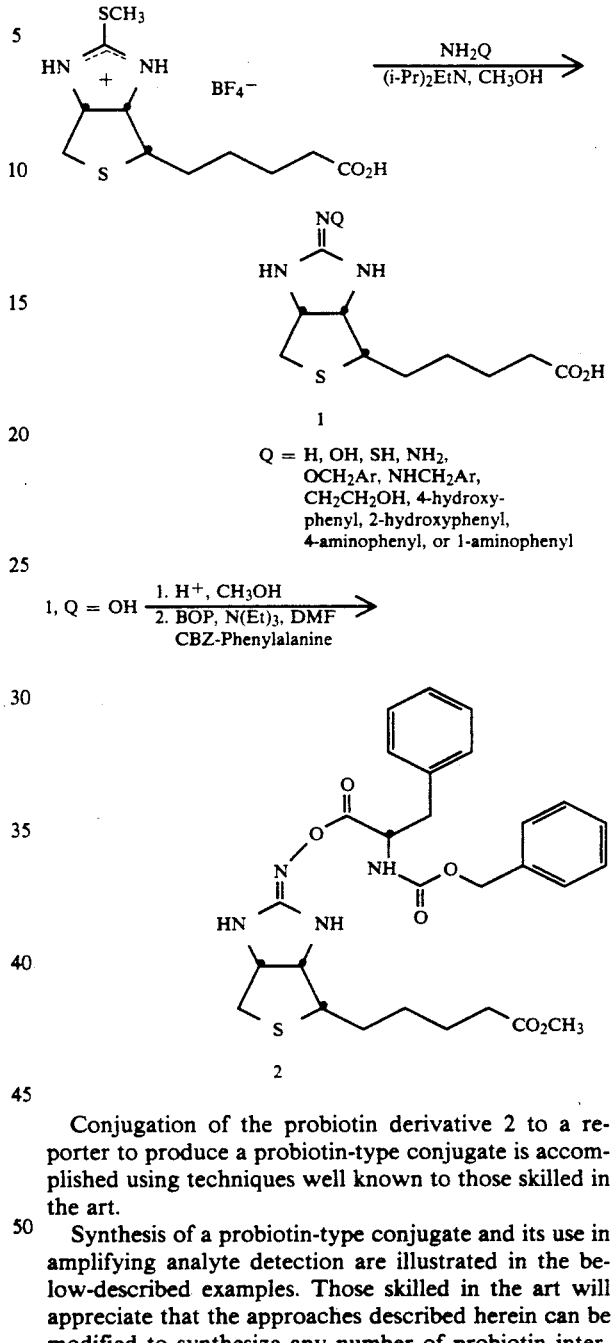

Probiotins can be synthesized generally according to the procedure described below. Oximinobiotin 1 (Q=OH) is an important intermediate for functionalizing the C2' position for activation by an ADEAS. The oxime oxygen or oximinobiotin can be functionalized affording means of attaching blocking groups, either with or without spacer arms, to the C2 position. For example, the probiotin substrate 2 containing a blocking functionality can be prepared by the following synthetic route:

Conjugation of the probiotin derivative 2 to a reporter to produce a probiotin-type conjugate is accomplished using techniques well known to those skilled in the art.

Synthesis of a probiotin-type conjugate and its use in amplifying analyte detection are illustrated in the below-described examples. Those skilled in the art will appreciate that the approaches described herein can be modified to synthesize any number of probiotin intermediates and conjugates using procedures well known to those skilled in the art.

Other small organic molecule/receptor combinations which could be modified by those skilled in the art to produce a bifunctional conjugate include analogues of haptens/antibodies, sugars and oligosaccharides/lectins.

As is shown in Table 1, a number of receptors are available. The choice of a receptor will depend upon the conjugate selected.

The optimal concentration of conjugate is determined according to the procedure explained in Example 1. Optimal concentrations will vary depending upon enzyme used in the ADEAS and substrate selected to produce conjugate.

Conjugate can be synthesized using conventional coupling and labeling techniques. Substrate choice will depend upon the ADEAS selected. To reiterate, detailed knowledge is required of the catalytic properties of each specific enzyme in order to properly design a useful synthetic substrate and, if necessary, a receptor.

A wide variety of reporters are available for coupling to the substrate to produce the conjugate or to couple to a member of a specific binding pair. As was discussed above reporter should introduce a different moiety to the substrate. Reporters can be a radioactive isotope, such as, $^{125}I$, enzymes, fluorogenic, light scattering, chemiluminescent, electrochemical or magnetic materials. Internally labeled reporters (e.g., tritium or other such radionuclides) which do not introduce a different moiety to the substrate are not contemplated for practicing the invention.

Examples of reporter enzymes which can be used to practice the invention include hydrolases, lyases, oxidoreductases, transferases, isomerases and ligases some preferred examples are phosphatases, esterases, glycosidases and peroxidases. Specific examples include alkaline phosphotase, lipases, beta-galactosidase, horseradish peroxidase and porcine liver esterase. As was noted above, if an enzyme is used as a reporter, it can be the same as or different from the enzyme or enzymes used in the ADEAS. The instant invention can be used to catalyze deposition of a radioisotopically labeled conjugate or an enzyme-labeled conjugate, etc.

Another embodiment of the forward sandwich immunoassay described above would involve reacting a capture-antibody-analyte-second antibody complex with an ADEAS consisting of an anti-antibody coupled to an enzyme such as HRP or AP. The anti-antibody would bind an epitope on the second antibody.

This invention is not limited to sandwich immunoassays. It is applicable to a wide variety of assay formats, for example, nucleic acid hybridization assays for both RNA and DNA.

To further illustrate the invention, examples of single and multi-enzyme ADEAS', conjugates, receptors, and receptor types are presented in Table 1 below.

TABLE 1

| Class | ADEAS Enzyme | CONJUGATE[2] Substrate | Class | RECEPTOR Type |
| --- | --- | --- | --- | --- |
| Single Enzyme | HRP[1] | Substituted phenols, e.g., tyramine | Endogenous | Phenols; electron rich moieties |
| Single Enzyme | HRP[1] | MBTH | Exogenous | DMAB |
| Single Enzyme | β-Galactosidase | β-Galactopyranosyl-glycoside, e.g., of fluorescein, coumarin, etc. | Exogenous | Antibody to deglycosylated moeity, e.g., anti-fluorescein; anti-coumarin |
| Single Enzyme | AP | NADP | Exogenous | NAD binding proteins |
| Single Enzyme | AP | Substituted phosphates, e.g., nitrophenyl phosphate | Exogenous | Antibody to dephosphorylated product, e.g., anti-nitro-phenol |
| Single Enzyme | AP | Phosphorylated biotin | Exogenous | Avidin; streptavidin |
| Multi-Enzyme | AP and HRP[1] | Phosphorylated substituted phenols, e.g., tyrosine phosphate | Endogenous | Phenols; eletron rich moieties |
| Multi-Enzyme | Neuraminidase and β-galactosidase | Sialyl-β-galactopyranosyl-glycoside of coumarin | Exogenous | Antibody to deglycosylated moiety, e.g., anti-coumarin |

[1]HRP requires the presence of $H_2O_2$.
[2]Label can be a reporter or member of a specific binding pair.

In the AP/HRP multi-enzyme ADEAS described above, the conjugate must be dephosphorylated before it will react with HRP; and in the β-gal/neuraminidase multienzyme ADEAS, the conjugate must be desialylated before it will react with β-gal.

It should be clear to those skilled in the art that a large number of variations are possible and all these variations fall within the scope of the invention.

The following examples are intended to illustrate the invention. Unless otherwise indicated, 100 µl of all reagents were used for the EIA strip assays. The one exception was that 200 µl of blocking buffer was used.

EXAMPLE 1

Preparation of Conjugates and Optimization of Conjugate Concentration

Para-hydroxyphenylpropionyl biocytin (HPPB) was prepared by mixing a solution of p-hydroxyphenylpropionic acid-N-hydroxysuccinimide ester (50 mg [0.2 mMol]/2 ml dimethyl sulfoxide) with biocytin (70.75 mg [0.2 mMol]/2 ml 0.1 M NaHCO₃) overnight at room temperature (RT). Biotin-tyramine (BT) was prepared by mixing a solution of tyramine (40 mg [0.3 mMol]/1 ml dimethyl sulfoxide) with biotin-N-hydroxysuccinimide ester (100 mg [0.3 mMol]/1 ml dimethyl sulfoxide) overnight at RT. The solutions of HPPB and BT were used as is. The calculated concentrations were 26 mg/ml for HPPB and 55 mg/ml for BT.

Polystyrene EIA strips (NUNC) were coated with polyclonal anti-Herpes Simplex Virus (HSV) antibody (Dako, Carpenteria, Calif.) in 0.1 M carbonate buffer pH 9.6 overnight at 4° C., and then blocked with 2% bovine serum albumin (BSA) in carbonate buffer and then washed with 10 mM phosphate buffered saline, 0.05% Tween 20, pH 7.4 (PBST). A dilution of HSV antigen in 1% BSA, 10 mM phosphate buffered saline, 0.05% Tween 20 pH 7.4 (BSA-PBST), or buffer without antigen, was incubated for 1 hour at 37° C. The dilution was sufficient to obtain the optical densities in the range reported in Table 1. It was washed with PBST. The analyte dependent enzyme activation system consisted of HRP coupled to anti-HSV (HRP ADEAS) which was purchased from Dako. The HRP ADEAS was added and incubated for 30 min. at RT and was washed with PBST. Various concentrations of HPPB or BT as set forth in Table 1 below, were added in 50 mM trisHCl, 0.01% $H_2O_2$, pH 8.0, for 15 min. at RT. After washing with PBST, streptavidin-HRP was added and incubated for 15 min. at RT to react with deposited biotins. The plate was then washed with PBST. An HRP substrate, o-ephenylenediamine (OPD), was added, incubated for 30 min. at RT, and stopped with 4 N $H_2SO_4$. Optical densities at 490 nm were recorded on a microtiter plate reader.

Results

Results are presented in Table 2. Column 1 presents the various concentrations in µl/ml of HPPB or BT. Columns 2 and 3 present the optical densities recorded as a function of HPPB concentration. Columns 4 and 5 present the results obtained using BT.

HPPB and BT were converted to activated forms by HRP ADEAS. Catalyzed reporter deposition was achieved without immobilizing a receptor.

In choosing the optimal concentration, one must look at both the magnitude of signal amplification as well as the signal to noise ratio. With this in mind, the optimal concentration of HPPB was 20 µl/ml (approximately 0.5 mg/ml), and that of BT, was about 0.3 µl/ml (approximately 16 µg/ml).

TABLE 2

| Conc. HPPB or BT (µl/ml) | Absorbance 490 nm | | | |
|---|---|---|---|---|
| | HPPB CONJUGATE | | BT CONJUGATE | |
| | HSV | Buffer (w/o Ag)* | HSV | Buffer (w/o Ag) |
| 0 | 0.079 | 0.031 | 0.079 | 0.031 |
| 20 | 1.155 | 0.181 | 0.700 | 0.165 |
| 10 | 0.904 | 0.140 | — | — |
| 5 | 0.499 | 0.120 | 2.060 | 0.430 |
| 2.5 | 0.177 | 0.063 | — | — |
| 1.25 | 0.113 | 0.062 | 2.230 | 0.502 |
| 0.625 | 0.103 | 0.048 | — | — |
| 0.313 | — | — | 1.880 | 0.169 |
| 0.078 | — | — | 0.263 | 0.051 |
| 0.020 | — | — | 0.090 | 0.040 |

*w/o Ag = without antigen

EXAMPLE 2

Amplification of Detector Signal In HSV Assay Using Catalyzed Reporter Deposition Anti-HSV coated EIA strips were prepared as described in Example 1. A 1:100 dilution of HSV antigen was prepared and serially four-fold diluted. These dilutions of HSV were incubated for 2 hours at 37° C. with the anti-HSV coated EIA strips. Excess reagent was washed off with PBST. The ADEAS as the same as that described in Example 1 above. It as added to the anti-HSV coated EIA strips containing the anti-HSV-HSV complex and incubated for 30 min. at RT and then washed with PBST. 20 µl/ml of HPPB conjugate as determined in Example 1 was added in 50 mM tris-HCl, 0.01% $H_2O_2$, pH 8.0, and was incubated for 15 min. at RT and then washed with PBST. Deposited biotins were reacted with streptavidin-HRP (SA-HRP) for 15 min. at RT. It was washed with PBST. The substrate, OPD, was added and incubated 30 min. at RT, stopped with 4 N $H_2SO_4$, and the absorbance at 490 nm was recorded on a microtiter plate reader.

Non-amplified assays were run in which (a) no HPPB and no SA-HRP were used; (b) HPPB was used without SA-HRP; (c) SA-HRP was used without HPPB.

Results

The results shown in FIG. 1 demonstrate that (a) catalyzed deposition of reporter was obtained and (b) both the conjugate and SA-HRP were needed for detection because the conjugate contained an unlabeled member of a specific binding pair.

Results for the non-amplified assay (no HPPB, no SA-HRP) were plotted. The results for the other assays were not plotted because the additional plots would overlap with the non-amplified results already plotted.

EXAMPLE 3

Synthesis of the Conjugate, HEE-6-AP, from (N-succinimidyl)-6-(phenoxy-(4'-azo-2''-carboxyethylphenyl)hexanoate, HEE-6-NHS, and Alkaline Phosphatase (AP)

Figure 2:
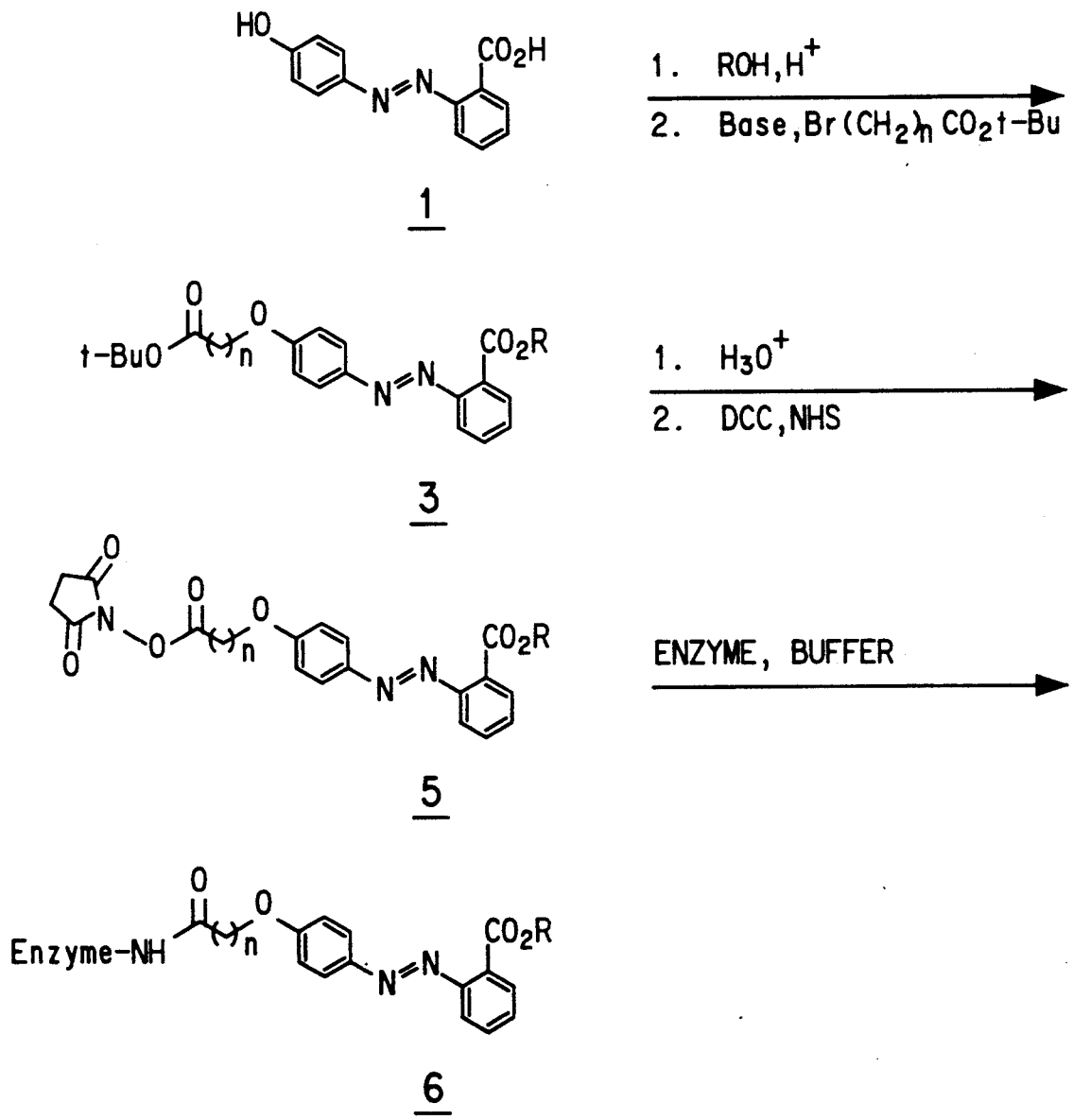
FIG. 2 depicts a preparation of ethyl 2-(4'-hydroxyphenylazo)benzoate-6-alkaline phosphatase (HEE-6-AP), the synthesis of which is described in Example 10.

The following reaction scheme is illustrated in FIG. 2: Ethyl 2-(4'-hydroxyphenylazo)benzoate (HEE), is prepared from 2-(4'-hydroxyphenylazo)-benzoic acid (HABA, (1)), anhydrous ethanol and a catalytic amount of acetyl chloride. The ethyl ester (HEE) is reacted with t-butyl 6-iodohexanoate and sodium hydride using the general procedure reported by Castellanos et al., Tetrahedron, pages 1691–1696, Vol. 37, (1981), to produce t-butyl-6-(phenoxy-(4'-azo-2''-carboxyethylphenyl)hexanoate (HEE-6-t-Bu, (3)). The tert-butyl ester is hydrolyzed by treatment with trifluoroacetic acid using the general procedure reported by Bryan et al., Journal of the American Chemical Society, pages 2353–2355, Vol. 99, (1977), to produce 6-(phenoxy-(4'-azo-2''-carboxyethylphenyl)-hexanoic acid (HEE-6-H). (N-succinimidyl)-6-(phenoxy-(4'-azo-2''-carboxyethylphenyl)hexanoate (HEE-6-NHS, (5)) is prepared from HEE-6-H, N-hydroxysuccinimide and dicyclohexylcarbodiimide in THF using the general procedure reported by Bryan et al., Makromolecular Chemie, pages 2375–2382, Vol. 186, (1985). The NHS ester (5) is dissolved in a minimum volume of DMSO and added to a buffered aqueous solution of alkaline phosphatase (e.g. calf intestine) using the general procedure reported by O'Sullivan et al., Methods in Enzymology, pages 147–166, Vol. 73, (1981) to give the conjugate (HEE-6-AP, (6)).

EXAMPLE 4

Synthesis of HABA-Tyramine Conjugate (H-T) from (N-succinimidyl)-6-(phenoxy-(4'-azo-2''-carboxyethylphenyl)hexanoate (HEE-6-NHS, (5)) and Tyramine The NHS ester (5) (1 mmol) described in Example 10 above, and tyramine (1 mmol) are dissolved in DMF (5 mL) and stirred at RT for 48 hrs. The solution is evaporated to dryness in vacuo. The residue is suspended in $H_2O$ (pH 8.0, 50 mL) and porcine liver esterase (100 mg) is added. The pH of the solution is maintained by adding 0.1 N NaOH as required. The solution is evaporated to dryness after 24 hours. The resulting H-T conjugate is isolated by chromatography (silica gel, chloroform/methanol).

EXAMPLE 5

Amplification of Detector Signal in a Mouse IgG Assay Using Porcine Liver Esterase (PLE) Catalyzed Reporter-Enzyme Deposition Microtiter plate strips (Nunc) are coated with a mixture of goat anti-mouse IgG (Fc fragment specific) antibody (ICN) and streptavidin (Scripps Laboratories) in 0.1 M carbonate buffer pH 9.6 overnight at RT. They are then blocked with 2% BSA in PBS and washed with PBST. Dilutions of mouse IgG (0–100 ng/mL) in BSA-PBST are incubated in the wells for 1 hr. at 37° C. followed by washing with PBST. A preparation of goat anti-mouse IgG-PLE (PLE ADEAS) (0.75 mg/mL) is prepared by the general method described by Hashida et al., Journal of Applied Biochemistry Vol. 6, pages 56–63, 1984 and diluted 1:100–1:2000 with phosphate buffer (0.1 M, pH 8.0, 0.2% BSA) and is incubated for 1 hr. at 37° C. and washed with PBST. HEE-6-AP (1 mg/mL) (prepared as described in Example 3) is added to the microtiter plate well and incubated for at least 15 min. at 37° C. The plate is then washed with PBST. Spectrophotometric detection is achieved after the addition of p-nitrophenyl phosphate. Reactions are stopped by the addition of 1 N NaOH. Optical densities at 405 nm are recorded on the microtiter plate reader. Amplification of detector signal in this example results from catalyzed reporter-enzyme deposition, i.e., PLE catalyzes deposition of HEE-6-AP where the receptor, streptavidin, has been immobilized on the microtiter plate surface.

EXAMPLE 6

Demonstration of the Enzyme Modulated Binding of a Blocked Binder

A suspension of porcine liver esterase was added (10 uL, 2860 U/mL, Cat. No. E3128, Sigma Chemical, St. Louis, Mo.) to a solution of ethyl 2-(4'-hydroxyphenylazo)benzoate (HEE) (0.25 mM) and streptavidin (0.2 mg/mL) in phosphate buffer (0.1 M, pH 8.0, 2mL). A second solution identical to the first was prepared which contained no streptavidin. The absorbance of the two solutions was measured at 500 nm as a function of time. FIG. 3 shows that the absorbance of the solution which contained no streptavidin decreased over time indicating hydrolysis of HEE to 2-(4'-hydroxyphenylazo)benzoic acid (HABA). The absorbance of the solution which contained streptavidin increased over time indicating the formation of the HABA:streptavidin complex, which is known to have a strong absorbance at 500 nm.

EXAMPLE 7 a) Preparation of 2'-Oximinobiotin from 2'-Thiobiotin-2'-S-Methyl Fluoroborate 2'-Thiobiotin-2'-S-methyl-fluoroborate[1] (3.0 g, 8.28 mmol), hydroxylamine hydrochloride (0.76 g, 10.93 mmol) and N,N-diisopropylethylamine (3.78 mL, 2.80 g, 21.70 mmol) were dissolved in anhydrous methanol (100 mL) and heated to 40° C. under $N_2$ for 20 H. The reaction was cooled to RT and filtered. The white precipitate was washed with ice cold methanol (1×20 mL and 1×10 mL) and dried in vacuo to give a white powder (2.68 g). The crude product was chromatographed on a Merck Science RP-18 Lichroprep column and eluted as follows: 0.1% trifluoroacetic acid (TFA)/water (800 mL); 0.1% TFA/water with 5% acetonitrile (800 mL); 0.1% TFA/water with 10% acetonitrile (800 mL) and 0.1% TFA/water with 20% acetonitrile (800 mL). Fractions containing the desired product were pooled and concentrated in vacuo to give 2'-oximinobiotin trifluoroacetate as a white powder (1.84 g, 4.93 mmol, 60% yield) mp 119°–120° C. (TFA salt): $^1$H NMR (DMSO-$d_6$) s 1.2–1.8 (m, 6H), 2.22 (t, J=7.2 Hz, 2H), 2.80 (d, J=12.9 Hz, 1H), 2.96 (dd, J=12.9 Hz, J=4.5Hz, 1H), 3.27(m, 1H), 4.55 (m, 1H), 4.72 (m, 1H), 8.83 (br s, 2H), 10.23 (br s, 1H), 11.26 (br s, 1H); MS (m/z) calcd for $C_{10}H_{17}N_3O_3S$ 259.0991, found 259.0967

(1) H. Flaster and H. Kohn, J. Heterocyclic Chem., 18, 1425–1436 (1981).

b) Preparation of 2'-Oximinobiotin Methyl Ester Trifluoroacetate from 2'-Oximinobiotin Trifluoroacetate To a suspension of 2'-oximinobiotin trifluoroacetate salt (0.70 g, 1.87 mmol) in anhydrous methanol (35 mL), was added acetyl chloride (0.25 mL) and the reaction stirred under nitrogen at RT for 24 H. The homogeneous solution was concentrated in vacuo to give 2'-oximinobiotin methyl ester trifluoroacetate as a white powder (0.712 g, 1.84 mmol, 98% yield) mp 134°–135° C. (TFA salt): $^1$H NMR (DMSO-$d_6$) s 1.3–1.8 (m, 6H), 2.32 (t, J=7.3 Hz, 2H), 2.81 (d, J=12.9 Hz, 1H), 2.94 (dd, J=12.9 Hz, J=4.70, 1H), 3.29 (m, 1H), 3.35 (s, 3H), 4.53 (m, 1H), 4.71 (m, 1H), 8.55–8.85 (m, 2H), 10.17 (s, 1H), 11.11 (br s, 1H); FAB MS (m/z) 274.12 (M+H).

c) Preparation of a Probiotin Derivative, N-CBZ-Phenylalanine Oximinobiotin Methyl Ester, from 2'-Oximinobiotin Methyl Ester Trifluoroacetate Oximinobiotin methyl ester trifluoroacetate salt (0.100 g, 0.258 mmol) and N-CBZ-1-phenylalanine (CBZ=carbobenzyloxy) (0.110 g, 0.366 mmol) were dissolved in dry DMF (10 mL). Benzyltriazol-1-yl-oxytrisphosphonium-hexafluorophosphate (BOP), (0.162 g, 0.366 mmol) and triethylamine (0.29 g, 0.40 mL, 2.87 mmol) were then added and the mixture stirred under $N_2$ for 4 H, then concentrated in vacuo. The solid was partitioned between EtOAc (20 mL) and sat'd NaHCO$_3$ solution (10 mL). The organic layer was washed with sat'd NaHCO$_3$ solution (2×10 mL) and sat'd NaCl solution (5 mL), dried over MgSO$_4$ and concentrated in vacuo. The resulting orange powder (107 mg) was dissolved in methanol/DMF (100:1) and chromatographed on a LH-20 column (3.5×40 cm) with methanol. Fractions containing the desired product were pooled and concentrated to 5 mL. Methanol (20 mL) was added and solution concentrated to ca. 5 mL. This procedure was repeated 4 times. The solution was cooled in a dry ice bath. The suspension was filtered and the solid washed with cold methanol and dried in vacuo to give white crystals (35.88 mg, 0.0647 mmol, 25% yield) mp 155°–156.5° C. (mixture of syn and anti isomers): $^1$H NMR (DMSO-$d_6$) s 1.2–1.8 (m, 6H), 2.31 (t, J=7.3 Hz, 2H), 2.60–2.70 (m, 1H), 2.75–2.95 (m, 2H), 3.55–3.57 (m, 3H), 4.26 (m, 1H), 4.35–4.55 (m, 3H), 4.96 (m, 2H), 6.25 (br s, 0.3H), 6.46 (br s, 1H), 6.75 (br s, 0.7H), 7.20–7.45 (m, 10H), 7.65–7.80 (m, 1H); FAB MS (m/z) 555.20 (M+H).

d) Preparation of a Probiotin-Type Conjugate

The probiotin methyl ester described above in Example 7 (c) is saponified with dilute NaOH to produce the probiotin carboxylic acid. The probiotin carboxylic acid is activated by reaction with dicyclohexylcarbodiimide (DCC) and N-hydroxysuccinimide to give the probiotin NHS ester which is used directly to form a conjugate with alkaline phosphatase using the standard conditions described by Ngo, T. T., Lenhoff, N. M. and Ivy, J. (1982) Applied Biochem. Biotech. 7, 443–454, and Hofmann, K. et al. (1978) J. Am. Chem. Soc. 100, 3585–3590.

e) Activation of the Probiotin Derivative, O-(N-CBZ-phenylalanyl)-2'-oximinobiotin Methyl Ester, by Lipase A solution of N-CBZ-phenylalanine oximinobiotin methyl ester (10.0 mg, 0.018 mmol) in distilled $H_2O$ (0.99 mL)/DMF (0.01 mL) was treated with lipase (candida cylindracea, 3 mg, ca. 2000 units) and analyzed by HPLC. After 1 H, the probiotin was cleaved to form N-CBZ-phenylalanine and oximinobiotin methyl ester. Control samples containing no lipase did not show evidence of cleavage. The crude reaction mixture caused a displacement of HABA from the HABA/avidin or HABA/streptavidin complexes, confirming that the oximinobiotin methyl ester was produced by the hydrolysis. Control reactions which did not contain lipase failed to displace the HABA from the HABA/avidin or HABA/streptavidin complexes. This shows that probiotin did not bind to avidin or streptavidin until activated, that is until it was converted to oximinobiotin methyl ester, by lipase.

f) Preparation of Lipase-Anitbody Conjugate Reagent

A mixture of 10 mg of affinity purified goat anti-mouse IgG antibody (H&L chain specific) is purchased from Jackson ImmunoResearch Laboratories Inc. (West Grove, Pa.) and mixed with 5 mg of purified candida cylindracea lipase (Sigma, St Louis, Mo.) in 1 ml of 0.1 M sodium phosphate buffer (pH 6.8) at 4° C. The mixture is centrifuged at 4000× g for 30 min at 4° C. The lipase antibody mixture is then dialyzed overnight against four exchanges of 0.1 M phosphate buffer (pH 6.8) at 4° C. The dialyzed lipase antibody is added to a 5 ml beaker with a magnetic stirring bar. With gentle stirring 0.05 ml of a 1% aqueous solution of glutaraldehyde (EM grade) is added slowly over a period of 5 min. The reaction mixture is then allowed to stand at room temperature for 3 hr and then 0.1 ml of ethanolamine (pH 7.0) is added to quench unreacted glutaraldehyde. After an additional 2 hours at room temperature, the conjugate preparation is dialyzed over night at 4° C. against three exchanges of PBS buffer. BSA is then added to the conjugate solution to a final concentration of 0.2% and the solution is stored at 4° C.

EXAMPLE 8

Amplification of Detector Signal in a Mouse IgG Assay Using Probiotin Reporter-Enzyme Deposition.

Polystyrene EIA Microtiter Strips (NUNC) are coated with a mixture (10 μg/ml) of goat anti-mouse IgG (Fc fragment specific) antibody (ICN) and streptavidin (10 μg/ml; Scripps Laboratories) in 0.1 M carbonate buffer pH 9.6. After incubating overnight at room temperature (RT), the solution is removed and strips blocked with a solution of 2% bovine serum albumin (BSA) dissolved in the above carbonate buffer. The strips are then washed free of excess reagents by rinsing three times with a 10 mM phosphate buffered saline solution, (pH 7.4), containing 0.05% Tween 20 (PBST). A range of concentrations of mouse IgG from 0, 0.001, 0.01, 0.1, 1.0 to 10 ng/well diluted in 1% BSA-PBST are then added to two sets of wells and are incubated at 37° C. for 1 hour followed by washing with PBST.

For probiotin conjugate amplification, to one set is added goat anti-mouse IgG lipase (ADEAS) in 1% BSA-PBST followed by incubation at 37° C. for 0.5 hour.

For the non-amplified assay, the second set is incubated with a goat anti-mouse IgG alkaline phosphatase (Boehringer Manneheim) conjugate in 1% BSA-PBST for 0.5 hour at 37° C. The wells are then washed with PBST.

Probiotin conjugate is deposited by adding a suitable amount of probiotin conjugate (prepared as described in Example 7d above) solution to the test wells containing goat anti-mouse IgG-lipase (ADEAS) and is incubated for 30 minutes at 37° C. The strips are then washed three times with PBST at 37° C. to remove unbound probiotin conjugate.

Spectrophotometric detection is achieved by addition of p-nitrophenyl phosphate solution (1 mg/ml) in 10mM diethanolamine (pH 9.5), 0.5 mM $MgCl_2$ buffer to both sets of test wells. After 15 min. at 37° C. color development is stopped by addition of 50 ul of 0.1 M EDTA and optical densities read at 405 nm in a microtiter plate reader (Molecular Devices Corp., Palo Alto, Calif.).

For the amplified assay, color development results from the ADEAS catalyzed deposition of probiotin-type conjugate wherever the receptor, streptavidin, has been immobilized on the microtiter plate surface. Color intensity obtained by using the amplified assay format is greater than the color intensity obtained using a conventional, non-amplified assay format.

What is claimed is:

1. A compound of the formula:

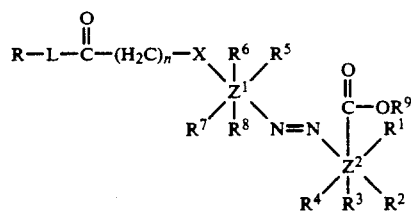

wherein:
  $R^1$ through $R^8$ are the same or different and are selected from the group consisting of H, OH, $OCH_3$, straight chain or branched alkyl groups having 1–4 carbon atoms, F, Cl, Br and;
  $Z^1$ and $Z^2$ are independently phenyl or napthyl;
  n is 1–19;
  X is N, O, S;
  $R^9$ is selected from the group consisting of glycosides and straight chain or branched alkyl groups having 1–4 carbon atoms;
  L is $(NH(CH_2)_sCO)_r$ where s is 1–5 and r is 0–5; and
  R is a reporter selected from the group consisting of radioisotopes, fluorogenic, light scattering, chemiluminescent, electrochemical and magnetic materials and enzymes provided that the enzyme does not react with $OR^9$.

2. A compound which is 6-(phenoxy-(4'-azo-2''-carboxyethylphenyl)-hexanoyl-alkaline phosphatase.

* * * * *